United States Patent

Heald et al.

[11] Patent Number: 6,096,553
[45] Date of Patent: Aug. 1, 2000

[54] ON-LINE ANALYSIS OF ACID CATALYST IN AN ALKYLATION PROCESS

[76] Inventors: Randall L. Heald, 209 Skycrest, Borger, Tex. 79007; Alan Dan Eastman, 3209 Wilson Rd., Bartlesville, Okla. 74006; Bruce B. Randolph, 233 Turkey Creek Rd., Bartlesville, Okla. 74006; Donald H. Renfro, 4342 SE. Adams, Bartlesville, Okla. 74006

[21] Appl. No.: 09/208,219

[22] Filed: Dec. 9, 1998

Related U.S. Application Data

[60] Provisional application No. 60/069,867, Dec. 17, 1997.

[51] Int. Cl.$^7$ .................................................. G01N 21/59
[52] U.S. Cl. .......................... 436/40; 436/60; 436/139; 436/171; 422/82.09; 250/339.12
[58] Field of Search ................ 436/55, 60, 61, 436/139, 40, 171; 422/62, 82.09; 250/339.12, 339.08, 339.01, 340

[56] References Cited

U.S. PATENT DOCUMENTS

| | | | |
|---|---|---|---|
| 3,935,097 | 1/1976 | Roof | 210/31 |
| 4,009,998 | 3/1977 | Benningfield, Jr. | 23/230 |
| 4,207,423 | 6/1980 | Makovec et al. | 422/111 X |
| 5,407,830 | 4/1995 | Altman et al. | 436/55 |
| 5,583,049 | 12/1996 | Altman et al. | 436/55 |
| 5,681,749 | 10/1997 | Ramamoorthy | 436/55 |

*Primary Examiner*—Jeffrey Snay
*Attorney, Agent, or Firm*—Richmond, Hitchcock, Fish & Dollar

[57] ABSTRACT

A computer implemented method for on-line determination of concentrations in an HF alkylation process catalyst stream containing HF acid, ASO, water and optionally an additive which suppresses the vapor pressure of HF acid. The method employs near-infrared spectroscopy coupled with chemometric data analysis. The data analysis uses a partial least squares regression technique which determines unknown concentrations based on spectral calibration data. In use, an absorbance spectrum of material is obtained, e.g., from a slipstream taken from the process alkylation catalyst stream, and the detected spectrum is mathematically analyzed with the aid of the computer to simultaneously predict concentration of HF acid, ASO, water and optionally the additive which suppresses the vapor pressure of HF acid.

11 Claims, 5 Drawing Sheets

ON-LINE ANALYSIS OF ACID CATALYST IN AN ALKYLATION PROCESS

This application claims the benefit of U.S. provisional application Ser. No. 60/069,867 filed Dec. 17, 1997.

The present invention relates to process analytical chemistry using near infrared spectroscopy, and more particularly to absorption of specific electromagnetic wavelengths by chemical components in a liquid acid catalyst mixture.

BACKGROUND OF THE INVENTION

Hydrogen fluoride (HF) alkylation is an important refinery process in which isobutane is reacted with olefins to produce highly-branched isoparaffins as illustrated in FIG. 1 for use in gasoline blending. In this process, hydrofluoric (HF) acid functions as the catalyst and recirculates through the reactor. The recirculating HF acid catalyst is not pure; it contains a small amount of water and a reaction byproduct called acid-soluble oil. The catalyst is also saturated with the hydrocarbons involved in the process (e.g., alkylate and isobutane). In the HF alkylation process, it is important to monitor and control the purity of the catalyst since excessive amounts of water and acid-soluble-oil (ASO) have deleterious consequences: Excessive water, for example, can cause rapid corrosion of some carbon steel components.

Controlling the activity of the catalyst requires measuring the concentrations of HF acid, water, and ASO in a recirculating catalyst stream. Therefore, prior to this invention operators would take samples of the catalyst periodically and have these components measured by classical analytical techniques. There are several problems associated with this approach. First of all, HF acid will cause serious burns if it contacts skin. Because of this hazard, collecting and analyzing these samples carries potential for injury. Another problem is that the analytical methods used for these measurements lack precision, especially the method for ASO. This often makes it difficult to determine if the composition of the catalyst has truly changed from sample to sample. Finally, samples are drawn from the reactor only once or twice a day, and the analyses require several hours. This makes it difficult to follow the composition of the catalyst in a timely manner when processing changes do occur.

In the past few years, there has been a great deal of interest in on-line monitoring of various refinery process streams. In part, this interest has been spurred by advances in analytical technology that have greatly expanded the capabilities for process monitoring.

Accordingly, it is an object of the invention to continuously analyze hydrocarbon process streams containing acid catalyst, ASO and water.

It is a more specific object of this invention to improve precision and reduce the time required for analytical chemistry measurements of acid catalyst, ASO and water.

Yet another object is to reduce exposure of refining personnel to hazardous process chemicals.

Still another more specific object of this invention is to detect relatively small changes in ASO and other impurities in a recirculating catalyst stream that result in reduced catalyst activity.

SUMMARY OF THE INVENTION

A method and apparatus for on-line process chemical analysis yields three-component concentration values in an alkylation catalyst stream, which is typically a mixture of acid catalyst, ASO, water, and hydrocarbons. In accordance with one aspect of the invention, the method involves using near-infrared spectroscopy in which a spectrometer/analyzer acquires spectral absorbance data of the recirculating catalyst in an alkylation process over a wavelength range of about 1250 nm to about 2200 nm. Within this spectral region appear absorption bands associated with each of the three components of interest e.g., HF acid has a strong broad absorption band with a maximum peak located at approximately 1390 nm. Likewise, water has an absorption band centered near 1935 nm. ASO has associated with it multiple sharp bands located between about 1670 nm and 1850 nm. According to the invention, determination of individual concentrations of components in the acid catalyst stream relies on a mathematical analysis of the entire acquired spectral region using a technique known as partial least squares regression. The determination of water concentration in an acid catalyst however, relies primarily on a specific band within the acquired spectral region in a range from about 1925 nm to about 1945 nm. The mathematical analysis of the spectral data, which is more fully described herein below, is one of a number of known multivariate analysis techniques, which are referred to collectively as chemometrics.

In accordance with another aspect of this invention a quadruple-component chemical analysis yields individual concentrations as indicated above, and additionally yields concentration of an additive to the recirculating acid catalyst stream which suppresses the vapor pressure of HF acid. The presently preferred additive is sulfolane, and in the quadruple measurement, the wavelength region measured contains additionally three narrow absorption bands associated with sulfolane. These bands are located near 1420 nm, 1725 nm, and 1920 nm.

The method and apparatus of this invention, using spectral absorption data in combination with chemometric analysis of the spectral absorption data, thus rapidly measure concentration of multiple components in a hazardous stream with very high precision. Further, the invention eliminates the need to manually collect samples from the reactor, and the essentially real-time analysis and high accuracy of the measurement allows operators and engineers to respond much more quickly to small changes in acid catalyst composition and/or activity.

Other objects and advantages of the invention will be apparent from the foregoing brief description of the invention and the appended claims as well as the detailed description of the drawings which are briefly described as follows:

DETAILED DESCRIPTION OF THE INVENTION

Near-Infrared Spectroscopy

Figure 1:
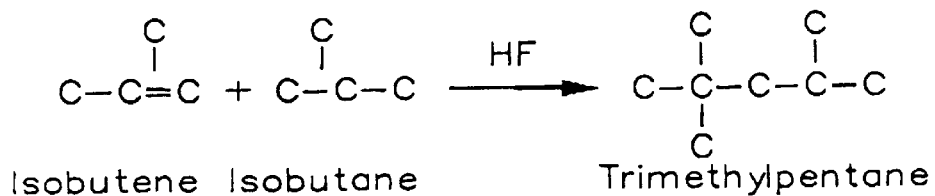
FIG. 1 is an illustration of a chemical reaction formula for producing an alkylate product.
Figure 2:
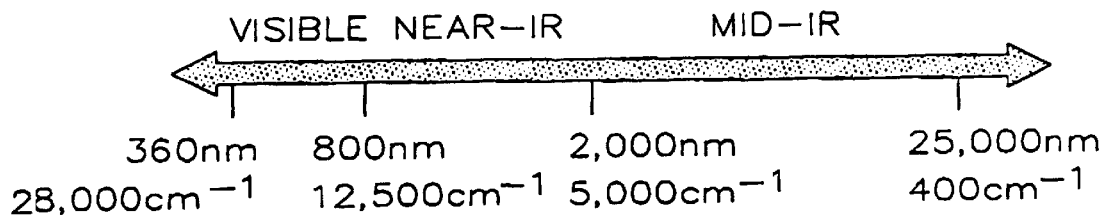
FIG. 2 is a graphical form for illustrating the NIR region of the electromagnetic spectrum.
Figure 4:
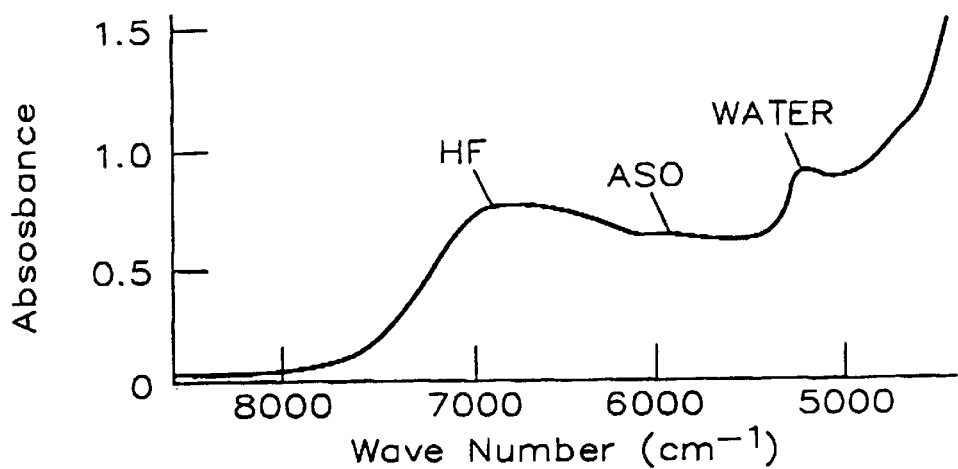
FIG. 4 is a graph showing the NIR absorbance spectrum of an HF process acid catalyst stream.

The method and apparatus described in this specification involves an analytical measurement technique based on near-infrared (NIR) spectroscopy, which uses electromagnetic radiation in the NIR region shown in FIG. 4 and in FIG. 2. This region of the spectrum lies between the visible region where our eyes function and the mid-infrared region where conventional infrared spectroscopy is performed.

Figure 3:
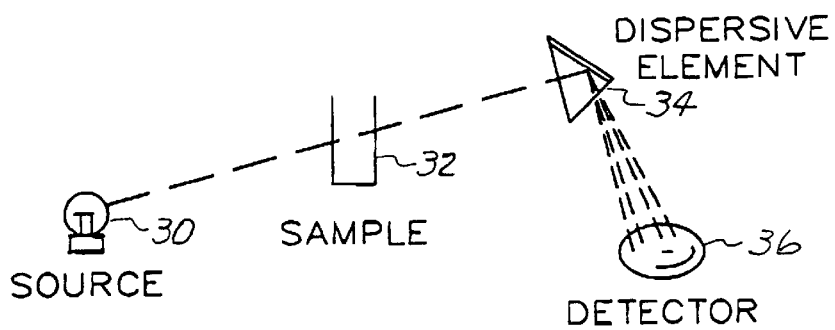
FIG. 3 is a schematic diagram illustrating key components used for NIR spectroscopy.

In NIR spectroscopy, as illustrated in FIG. 3, the radiation from a halogen lamp 30 is caused to pass through a sample contained in a cell 32. In on-line process analysis, the sample is from the process and can flow continuously through the cell. After the radiation passes through the sample, it is dispersed into its various wavelengths by a dispersive element illustrated at 34. Alternatively, in the case of Fourier transform spectroscopy, the radiation is modulated by an interferometer. Next, the dispersed or modulated radiation is detected at the detector 36. Finally, the detector signal is mathematically converted into a spectrum in which the amount of radiation absorbed is plotted as function of wavelength. Such an absorbance spectrum is illustrated in FIG. 4.

As in mid-IR spectroscopy, NIR spectra reflect the chemical structure of the compound(s) measured. In other words, each different chemical will have a characteristic absorption spectrum. NIR measurement times are fast, with results typically updated every one to three minutes, and NIR spectroscopy is inherently very precise. This is very important in process monitoring where detecting small changes in the process and following the associated trends is often of primary interest. NIR instrumentation optics are very rugged, and instruments often have only one moving part. In addition, robust optic materials such as quartz and sapphire can be used in the optical sections. Compatibility with quartz optics allows optical fibers to be used to convey NIR radiation from the spectrometer to a remote sample point. This provides a great deal of flexibility in how the analyzer is interfaced with the process. Optical multiplexing can be used in conjunction with fiber optics to monitor several sampling points with the same spectrometer. The combination of all of these features makes NIR spectroscopy one of the best analytical techniques for on-line process monitoring. A suitable on-line process analyzer for Fourier transform—IR application, is available from a company called Applied Automation Inc. (AAI), Inc. Bartlesville, Okla. 74004. This analyzer includes software that controls the sampling system, cell washing etc., in addition to obtaining spectral data.

Chemometrics

Referring now to FIG. 4, the NIR absorption spectrum of a typical HF acid catalyst is illustrated. FIG. 4 also illustrates the principal difficulty associated with the use of NIR spectroscopy. This spectrum contains absorption features that are associated with each of the components of interest i.e., HF, ASO, and water. Unfortunately, these bands are broad and overlap extensively. This overlap precludes the use of simple univariate calibration methods for quantitation of the sample components. This problem can be overcome by applying more powerful multivariate mathematical calibration techniques to the analysis of the spectral data. These multivariate mathematical techniques when applied to process chemical analysis are collectively referred to as chemometrics. As used herein chemometrics is the science of relating measurements made on a chemical system to the state of that system via the application of mathematical or statistical methods. This technique uses complex mathematics such as matrix vector algebra and statistics to extract quantitative information (i.e., concentrations) from highly convoluted or statistically confounded data. Chemometric analysis is typically performed in suitable high speed computers running commercially available software programs. Numerous software packages are currently available, for example, a program called "Pirouette" can be obtained from Infometrics, Inc., P.O. Box 1528 Woodinville, Wash. 98072. Pirouette is actually a suite of chemometric programs, including such methods as K-Nearest Neighbors analysis (KNN), Heirarchical Cluster Analysis (HCA), Principal Component Analysis (PCA), Partial Least Squares (PLS) analysis, and Principal Component Regression (PCR) analysis. Of these various data analysis methods, the first three are designed for pattern recognition and data classification. Only the last two, PLS and PCR are designed for constructing a calibration model and applying it to an instrument response (e.g., an NIR spectrum) to calculate a property of a sample (e.g., concentration of a chemical constituent). Of these two, PLS is most commonly applied to NIR spectral data because it generally provides the best calibration models in terms of accuracy.

Figure 6:
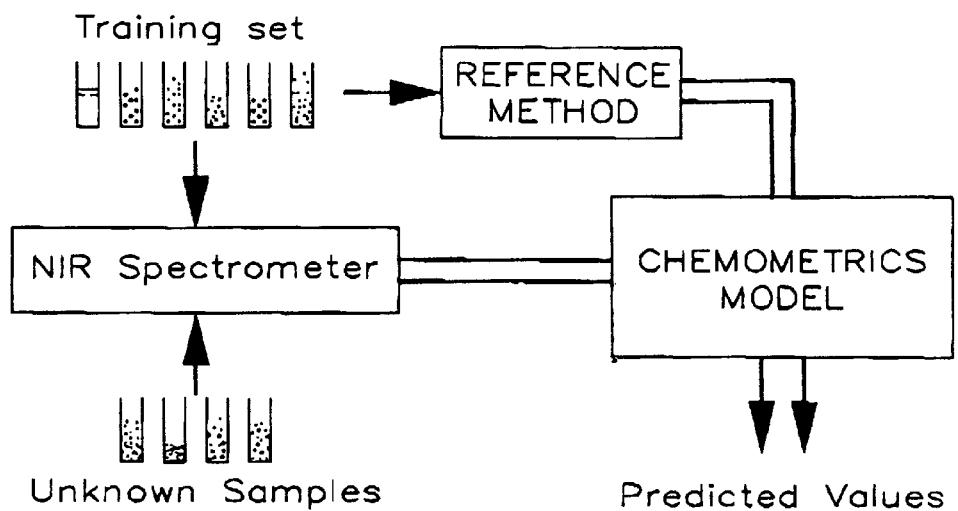
FIG. 6 is a schematic diagram illustrating how NIR spectroscopy and chemometrics function together.

In practice, quantitative NIR analysis using chemometrics requires fairly extensive calibration. This calibration is achieved by analyzing a set of samples with known values for all of the properties to be measured by NIR. These calibration samples are frequently characterized by a reference measurement method. In cases where the composition of the sample is relatively simple or the reference method suffers from poor precision, synthetic blends can be used for calibration. Regardless of how the properties are determined, the calibration sample set is generally referred to as the training set. The results for the training set (i.e., the NIR spectra and reference data) are used to build a calibration model using the multivariate calibration procedure. Once a suitable model is built, it is used to calculate the property or properties of interest from the NIR absorption spectra of unknown samples. This entire calibration process is diagramed in FIG. 6. Although somewhat complex, when properly executed this approach can be accurate, precise and robust.

For a discussion of chemometric techniques see, for example, Sharaf, M. A. Illmaen, D. L. and Kowalski, B. R., "Chemometrics", Wiley, New York, 1986.

Analyzer Configuration

Figure 5:
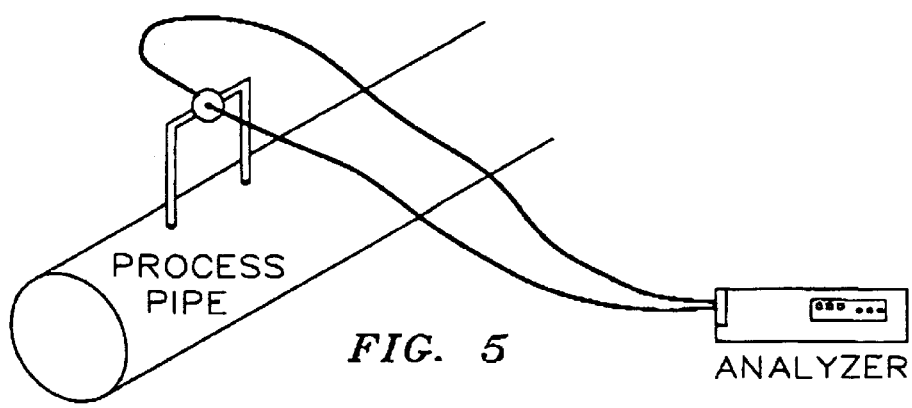
FIG. 5 is a schematic diagram illustrating an NIR analyzer interfaced to a process stream.

NIR analyzers can be interfaced with a process in a wide variety of configurations. One approach is shown in FIG. 5.

In this approach, the sample cell is located in a slip stream, and thus sample conditioning such as filtering and thermostating is possible prior to the analysis. Using an optical fiber interface maintains the ability to locate the analyzer in a remote location.

EXAMPLE 1.

Figure 7:
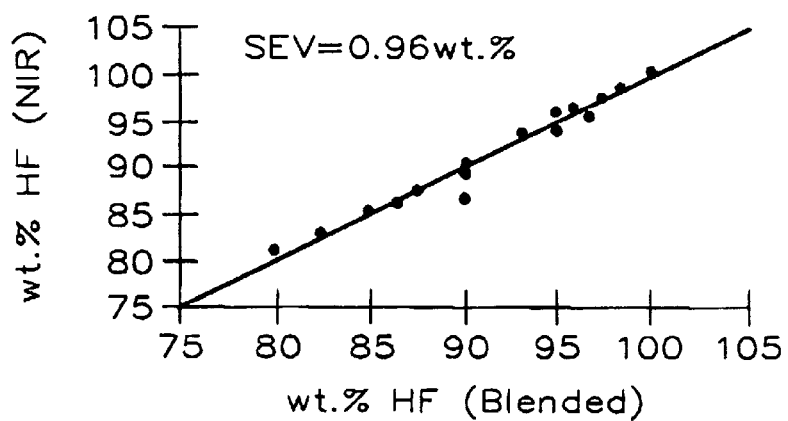
FIG. 7 is a graph illustrating actual blended concentrations versus NIR measured concentration for HF acid in a blended mixture of three components.
Figure 8:
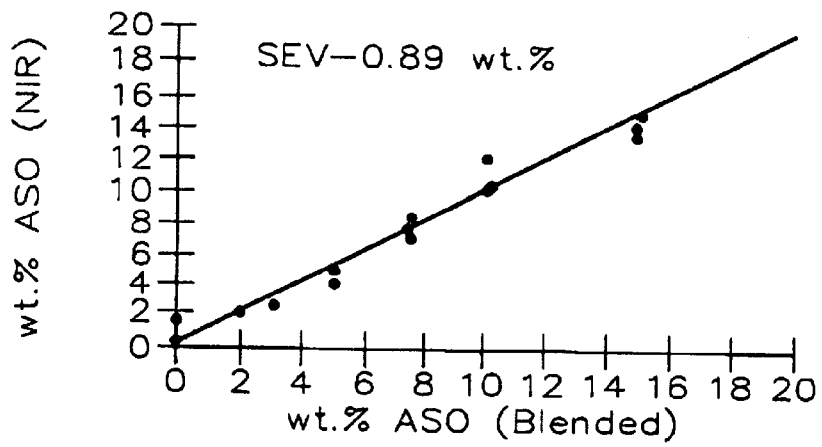
FIG. 8 is a graph similar to FIG. 7 showing measured concentration of ASO.
Figure 9:
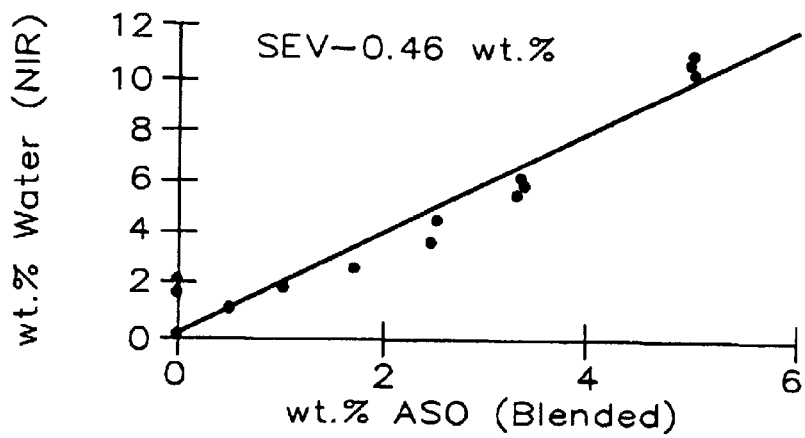
FIG. 9 is a graph similar to FIG. 7 showing measured concentration of water.

This example successfully demonstrates in a laboratory environment the feasibility of measuring three components including HF acid, ASO, and water contained in an HF process catalyst stream. FIGS. 7–9 show the correlations between the concentrations of these components calculated from the NIR data and the corresponding gravimetrically blended concentrations. In these figures, each NIR data point is the result of a cross-validation analysis, which is performed as follows: One at a time, each sample in the training set is excluded from the calibration set. A chemometric model is created from the remaining sample data. This model is then used to calculate the concentration (e.g., wt % HF acid) associated with the excluded sample. The excluded data is returned to the calibration set and another sample is excluded. A new model is generated and used to calculate a new result and error (difference between calculated result and known value). This leave-one-out process is continued for every sample in the training set.

The accumulated errors from the cross-validation analysis are used to calculate a standard error of cross validation (standard deviation of the errors), SEV. The SEV for each measured component is listed in upper left-hand corner of FIGS. 7–9. These values represent the standard deviations between the NIR and the blended concentrations, which were used as standard values, and thus reflect the accuracy of the NIR method. The demonstrated accuracy is very good for all three components.

Although agreement between the on-line analyzer and the laboratory methods is necessary, precision is more important in most applications. This is true because measurement precision determines just how small a process change can be reliably detected. As Table I below shows, the NIR method's precision is outstanding compared to the previously used lab methods. For each of the three components, the repeatability of the NIR measurement shows a 30- to 50-fold improvement over that of the corresponding lab method.

TABLE I

Measurement Precision Comparison

| Component | NIR | Lab Method |
|---|---|---|
| HF Acid | 0.1% | 3% |
| ASO | 2% | 80% |
| Water | 0.5% | 30% |

Figure 10:
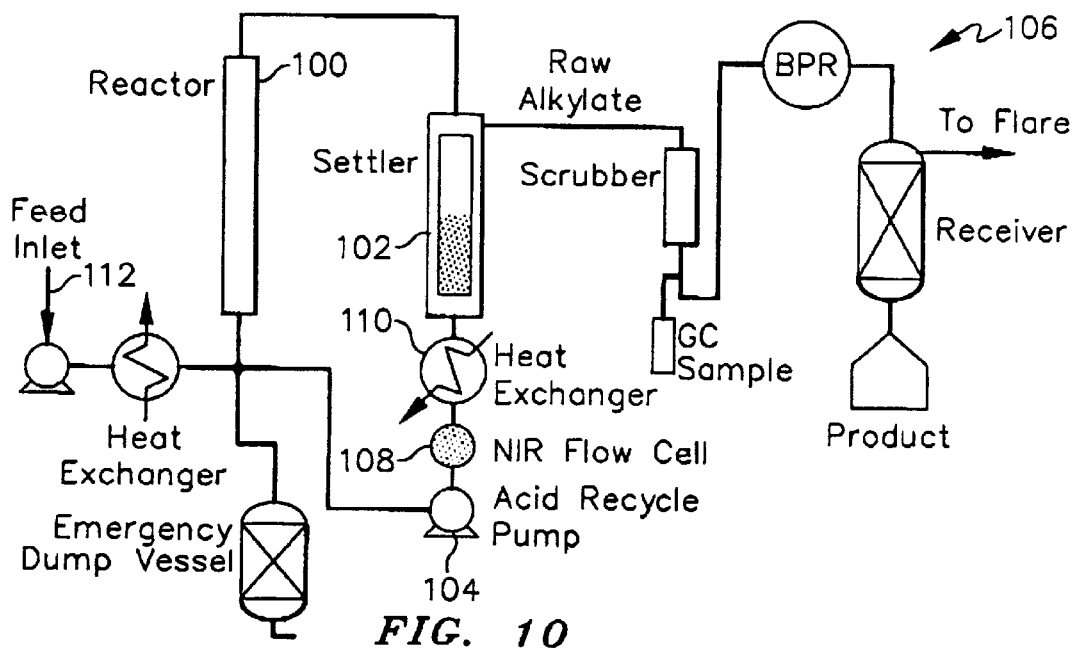
FIG. 10 is illustrating a lab scale reactor system for simulating a commercial alkylation process.

All calibration runs were carried out using a bench-scale riser reactor with a settler and acid catalyst recirculation as shown in FIG. 10. The sample cell used for all spectroscopic measurements was installed between the acid catalyst heat exchanger and the recirculation pump. For each calibration run, known amounts of HF, water, and ASO were blended and transferred to the reactor. Refinery alkylate and isobutane were added to the reactor and the material was recirculated under conditions similar to those found in the full-scale alkylation process.

An Applied Automation Advance FTIR Analyzer was used for all NIR spectroscopic measurements. The sample cell was constructed of Hasteloy-C with sapphire windows. The analyzer was coupled to the sample cell using low-OH quartz optical fiber. The spectral data was processed using a partial least squares algorithm available in the commercial chemometric software. The experimental design included 16 gravimetric blends that spanned a concentration range greater than that normally encountered in an actual alkylation unit. Table II below lists the concentration ranges for each of the three components.

TABLE II

NIR Calibration with 16 Gravimetric Blends

| Component | RANGE |
|---|---|
| HF Acid | 80–100 wt. % |
| ASO | 0–15 wt. % |
| Water | 0–5 wt. % |

EXAMPLE 2

The laboratory scale alkylation unit used in the previous example is illustrated in FIG. 10 and is more fully described below. This laboratory unit includes a riser reactor 100, a feed dispersion device which is not illustrated, an acid settler 102, an acid recirculation pump 104, and product collection equipment generally illustrated at 106. The same equipment was used in this example to successfully demonstrate laboratory scale operation at simulated process conditions. The NIR data were collected with a flow cell 108 mounted between the acid heat exchanger 110 and acid pump 104, such that all of the acid inventory flows through the cell 108 during each pass around the reactor. For each run, a pre-blended feed of olefins and isobutane was introduced to the reactor via the feed inlet 112. Starting acid concentration was 98% HF acid and starting water was 2% by weight. The acid/hydrocarbon emulsion from the reactor 100 is routed to the settler 102, where the acid phases out to the bottom and is recirculated to the reactor. Product hydrocarbon is withdrawn from the top of the settler 102, and then scrubbed to remove any HF acid, and then collected for analysis. Acid samples are withdrawn intermittently for HF acid and ASO determination to provide a comparison for NIR values.

Selected results for Run #1 are given in Table III below. The feed to the reactor 100 is a blend of refinery supplied olefins and isobutane. A feed introduction device is installed in order to increase the amount of ASO produced over that normally observed. This allowed enough ASO to be generated for a good comparison between NIR and standard techniques.

TABLE III

NIR and Traditional Acid Test Results: MTBE-Free Feed

| TOS* (Hours) | 20 | 44 | 68 | 92 |
|---|---|---|---|---|
| % HF (titration) | 89.3 | 93.0 | 86.6 | 88.4 |
| % ASO (extn) | 0.85 | 1.25 | 2.09 | 2.52 |
| % H2O (NIR) | 1.80 | 2.00 | 2.19 | 2.06 |
| TOTAL | 92.0 | 96.3 | 90.9 | 93.0 |
| % HF (NIR) | 91.81 | 90.22 | 88.69 | 88.01 |
| % ASO (NIR) | 0.391 | 1.78 | 3.12 | 3.92 |
| % H2O (NIR) | 1.80 | 2.00 | 2.19 | 2.06 |
| TOTAL | 94.0 | 94.0 | 94.0 | 94.0 |

*Time On Stream

Figure 11:
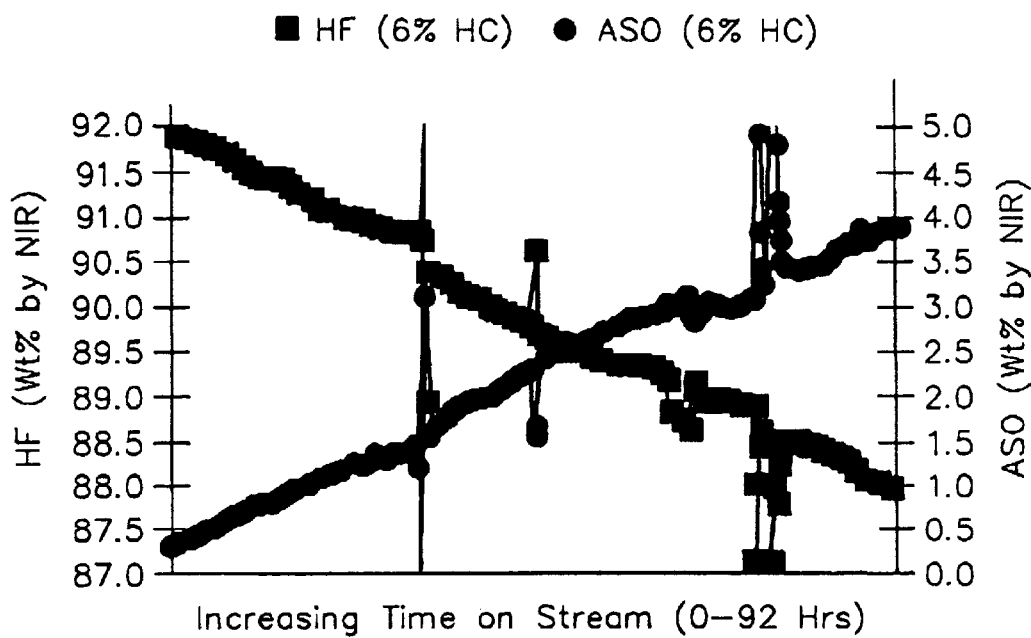
FIG. 11 is a graph illustrating concentration of HF acid and ASO versus time on stream in an alkylation process.
Figure 12:
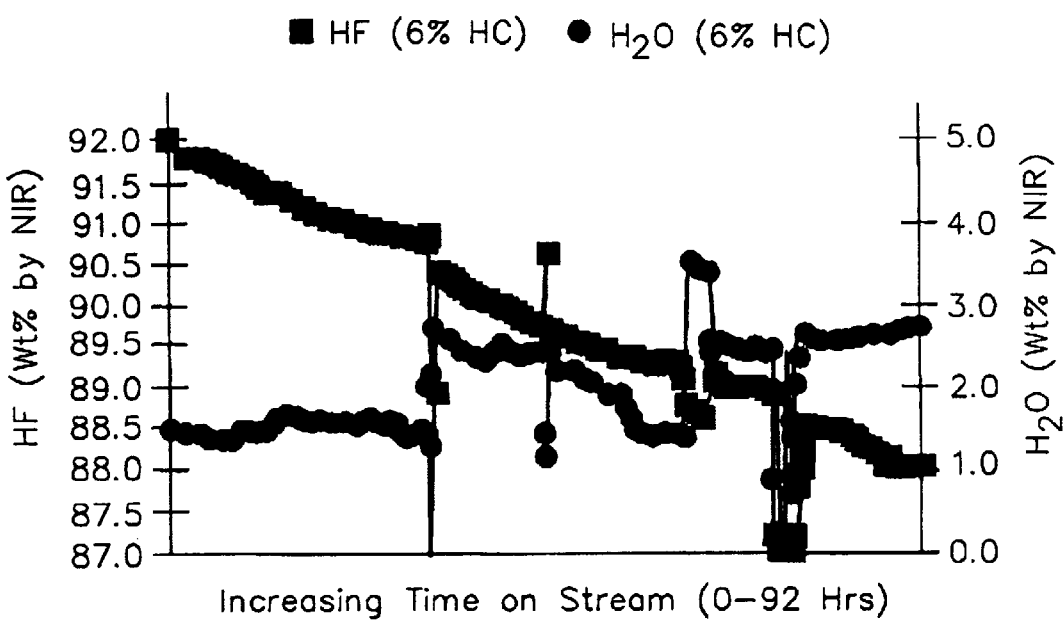
FIG. 12 is a graph illustrating concentration of HF acid and water versus time on stream in an alkylation process.

Standard HF titrations (dilution and titration to phenolpthalein endpoint) generally gave values within 2–3 wt % of the NIR values. The ASO concentrations determined by extraction (after neutralization) were usually only 50–70% of the NIR values. This was expected, however, because the NIR measures total ASO, while the extraction measures mostly heavier ASO (vide infra). Water was not analyzed by an independent method; however, the concentrations determined by NIR varied only within a fairly narrow range (1.8 and 2.2 wt %). FIGS. 11 and 12 show the trend lines associated with HF, ASO, and water versus increasing times on stream.

Figure 13:
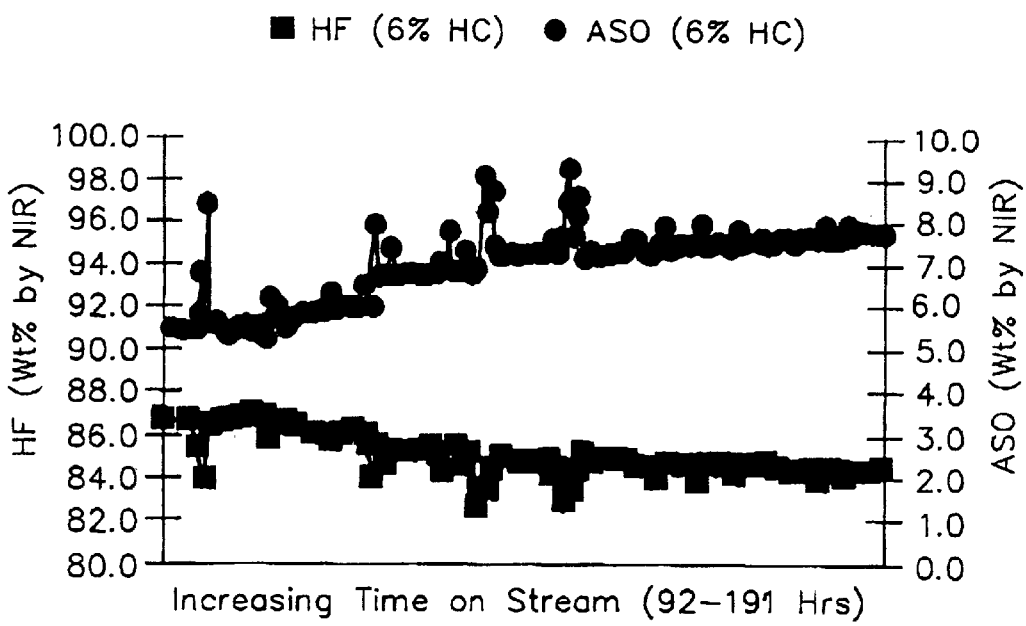
FIG. 13 is a graph similar to FIG. 11 illustrating extended time on stream.
Figure 14:
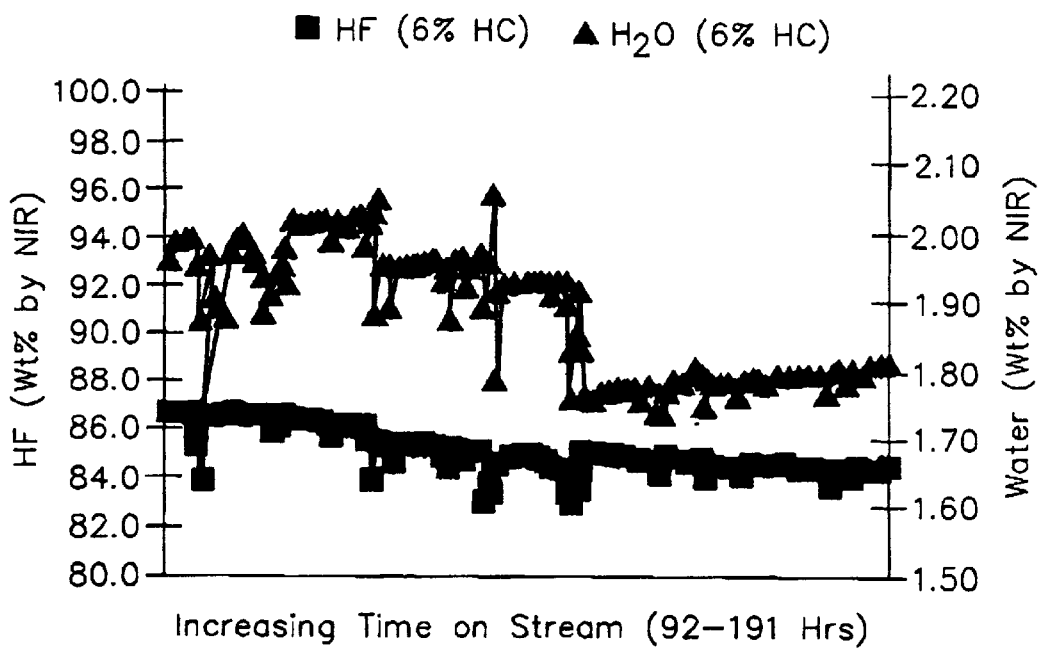
FIG. 14 is a graph similar to FIG. 12 illustrating extended time on stream.

After 92 hours, the feed was spiked with 570 ppm MTBE (methyltert-butylether) (or~7000 ppm based on olefin only). MTBE is commonly produced upstream of the alkylation unit as an oxygenate for RFG (reformulated gasoline). Under normal operation the concentration of MTBE in the alkylation feed is nil, but under upset conditions, levels of 1000–5000 ppm are possible and can have rapid, deleterious consequences for acid purity due to accelerated ASO production. Table IV gives the results for the acid analysis at selected times on stream. Again the HF acid concentration values from NIR are within 1–2 wt % of the titration values. Note the 70% increase in ASO concentration between 92 hours (Table III) and 113 hours (Table IV), reflecting the high propensity for ASO production from MTBE. The increase in ASO based on traditional data was only about 33%. Both the NIR and traditional concentration data show an increase in ASO with time, but again with traditional tests we observed only about 50–65% of the total ASO determined by NIR. Water remained relatively constant until acid purity was increased after 167 hours. At this time, the catalyst was nearly deactivated, necessitating a reduction of ASO and water and an increase in HF concentration. FIGS. 13 and 14 show the trend lines for HF, ASO, and water with the MTBE-containing feeds.

TABLE IV

NIR and Traditional Acid Test Results: 570 ppm MTBE-Feed

| TOS (Hours) | 113 | 143 | 167 | 191 |
|---|---|---|---|---|
| % HF (titration) | 87.3 | 86.4 | 84.2 | 86.0 |
| % ASO (extn) | 3.35 | 4.0 | 4.7 | 4.7 |
| % H2O (NIR) | 2.01 | 2.08 | 2.01 | 1.78 |
| TOTAL | 92.7 | 92.5 | 90.9 | 92.5 |
| % HF (NIR) | 85.3 | 84.4 | 83.3 | 85.0 |
| % ASO (NIR) | 6.71 | 7.51 | 8.73 | 7.28 |
| % H2O (NIR) | 2.01 | 2.08 | 2.01 | 1.78 |
| TOTAL | 94.0 | 94.0 | 94.0 | 94.0 |

One of the key advantages of NIR is the fast response time, and in the present work, spectra were taken every six minutes (times as short as 1 spectrum per minute are possible). The inherent precision of NIR is another significant advantage, showing a 30- to 50-fold improvement in repeatability when compared to the traditional laboratory test methods for HF, water, and ASO. The current technique allows the rapid determination of HF, ASO, and water directly and independently of each other, in the presence of other dissolved/dispersed non-ASO hydrocarbons such as C3, iC4, nC4, C5+ alkylate, etc. This is a result of the method in which the training set data were collected. The NIR results add to 94% since the raw data was normalized to reflect the usual rule of 6% hydrocarbon dissolved/dispersed in the acid phase. In all cases, the sum of the raw data for HF acid, ASO, and water was between 99.6 and 100.1%, even though the chemometric model was not constrained to limit that result. In traditional analyses, the difference between 94% and the sum of the acid components is taken as an indication of light ASO. As these data show, the traditional tests give an indication of about 1–3% light ASO (the titration value of 93% at 44 hours is likely an outlier). The NIR technique is set up (by design) to measure both light and heavy ASO. This is the reason for the discrepancy between NIR predictions and extraction measurements. Lighter ASO components are frequently lost during sample preparation for traditional tests.

The "spikes" present in FIGS. 11–14 occurred when acid was either added to or withdrawn from the reactor. These spikes in the trend lines result from the formation of gas/vapor bubbles which form inside the cell. Nitrogen is used as a pressure source for acid addition and to also maintain constant unit pressure. Accordingly, as acid is withdrawn or added, a pressure differential results. The cell, which is located between the acid cooler 110 and the magnetically driven acid recirculation gear pump 104, is susceptible to N2 gas bubble formation in the acid line. If bubbles develop, they can easily be trapped in the cell, since all of the acid in the system is routed through the cell. The gas bubbles cause rapid changes in the optical pathlength, resulting in wildly fluctuating values. The bubbles could be removed from the system by manipulation of the acid flow rate. Accordingly gas/vapor bubble formation is a phenomenon related to the experimental set-up in the laboratory.

While this invention has been described in terms of the presently preferred embodiment for on-line analysis of four components including HF acid, ASO, water and sulfolane in an HF alkylation process, the same analyzer might be used to analyze other process streams. In an alkylation process, a number of other measurements could be made. These might include concentration measurements of the alkylate product as well as the isobutane and olefin feed stream.

For the alkylate product stream, it is common practice to periodically sample and measure the research octane number (RON) as well as concentration of trimethylpentanes (TMP's) and dimenthylhexanes (DMH's), and these variables can be measured with excellent results using NIR techniques. NIR could also be used to monitor the isobutane-to-olefin ratio in the feed or the purity of the isobutane recycle stream.

Accordingly, reasonable variations and modifications are possible by those skilled in the art, and such modification and variations are within the scope of the described invention and the appended claims.

That which is claimed is:

1. A method for on-line concentration determination of at least three components in a liquid mixture which contains unknown concentrations of an acid catalyst for hydrocarbon conversion, an acid-soluble-oil (ASO), and water, said method for three component determination comprising the following steps:

(a) recording an electromagnetic absorbance spectrum for said liquid mixture over the near-infrared wavelength range of from about 1250 nm to about 2200 nm;

(b) using data from said absorbance spectrum in a chemometric analysis for determining concentration of said acid catalyst, and said ASO in said liquid mixture; and (c) using primarily that portion of data from said absorbance spectrum in a range of from about 1925 nm to about 1945 nm in said chemometric analysis for determining concentration of water in said liquid mixture.

2. A method in accordance with claim 1, wherein said liquid mixture is obtained in a slip stream from a recirculating acid catalyst stream in a hydrocarbon conversion process and wherein said liquid mixture comprises a flowing sample stream.

3. A method in accordance with claim 1, wherein said acid catalyst comprises hydrogen fluoride (HF) acid.

4. A method in accordance with claim 1, wherein said liquid mixture additionally contains an additive and said method for on-line concentration determination comprises a quadruple component concentration determination additionally including the following step:

using data from said absorbance spectrum in a chemometric analysis for determining concentration of said additive in said liquid mixture.

5. A method in accordance with claim 4, wherein said additive comprises sulfolane.

6. A method in accordance with claim 1, wherein said electromagnetic absorbance spectrum is obtained with a spectrometer/analyzer calibrated with a training set of gravimetrically blended samples, and wherein said spectrometer/analyzer is calibrated using a leave-one-sample-out technique.

7. A method in accordance with claim 1, wherein said chemometric analysis is carried out in a computer programmed with a chemometric model for determination of said at least three components.

8. Apparatus for on-line concentration determination of at least three components in a liquid mixture which contains unknown concentration of an acid catalyst for hydrocarbon conversion, an acid-soluble-oil (ASO), and water, said apparatus comprising:

(a) means for recording an electromagnetic absorbance spectrum for said liquid mixture over the near infrared wavelength range from about 1250 nm to about 2200 nm;

(b) computer means for using data from said absorbance spectrum in a chemometric analysis for determining concentration of said acid catalyst and, said ASO in said liquid mixture; and (c) computer means for using primarily that portion of data from said absorbance spectrum in a range of from about 1925 nm to about 1945 nm in said chemometric analysis for determining concentration of water in said liquid mixture.

9. Apparatus in accordance with claim 8 additionally comprising:

a sample cell; and a slip stream means for obtaining said liquid mixture from a recirculating acid catalyst stream in a hydrocarbon conversion process, and passing said liquid mixture to said sample cell.

10. Apparatus in accordance with claim 8, wherein said liquid mixture additionally contains an additive and said apparatus for on-line prediction comprises a quadruple component concentration prediction, said apparatus additionally including:

computer means using data from said absorbance spectrum in a chemometric analysis for determining concentration of said additive in said liquid mixture.

11. Apparatus in accordance with claim 8, wherein said means for recording said electromagnetic absorbance spectrum for said liquid mixture comprises a spectrometer/analyzer, said apparatus additionally comprising:

means for calibrating said spectrometer/analyzer comprising a training set of gravimetrically blended samples, and wherein said computer means is programmed with a chemometric model for determination of said at least triple components responsive to said recorded electromagnetic absorbance spectrum.

* * * * *